US011052222B2

(12) United States Patent
Engel et al.

(10) Patent No.: US 11,052,222 B2
(45) Date of Patent: Jul. 6, 2021

(54) SLEEP INDUCTION DEVICE AND METHOD FOR INDUCTING A CHANGE IN A SLEEP STATE (71) Applicant: Somnox Holding B.V., Delft (NL)

(72) Inventors: Job Engel, Delft (NL); Julian Jagtenberg, Delft (NL); Wouter Kooyman van Guldener, Delft (NL); Stijn Antonisse, Delft (NL)

(73) Assignee: Somnox Holding B.V., Delft (NL)

( * ) Notice: Subject to any disclaimer, the term of this patent is extended or adjusted under 35 U.S.C. 154(b) by 0 days.

(21) Appl. No.: 16/500,136

(22) PCT Filed: Apr. 3, 2018

(86) PCT No.: PCT/NL2018/050203
§ 371 (c)(1),
(2) Date: Oct. 2, 2019

(87) PCT Pub. No.: WO2018/186739
PCT Pub. Date: Oct. 11, 2018

(65) Prior Publication Data
US 2020/0338303 A1 Oct. 29, 2020

(30) Foreign Application Priority Data

Apr. 4, 2017 (NL) .................................. 2018645
May 10, 2017 (NL) .................................. 2018883

(51) Int. Cl.
A61M 21/02 (2006.01)
A47G 9/10 (2006.01)
A61M 21/00 (2006.01)

(52) U.S. Cl.
CPC .............. A61M 21/02 (2013.01); A47G 9/10 (2013.01); A61M 2021/0022 (2013.01);
(Continued)

(58) Field of Classification Search
CPC .......... A61M 21/02; A61M 2021/0022; A61M 2021/0088; A61M 2230/06; A61M 2230/42; A47G 9/10
(Continued)

(56) References Cited

U.S. PATENT DOCUMENTS 7,041,049 B1    5/2006 Raniere
2006/0102171 A1* 5/2006 Gavish ................... A61B 5/486
                                                     128/95.1
(Continued)

FOREIGN PATENT DOCUMENTS

JP    2007-512086 A    5/2007
JP    2016-515460 A    5/2016
(Continued)

OTHER PUBLICATIONS

Netherlands Search Report, Application No. 2018883, dated Oct. 24, 2017.
(Continued)

Primary Examiner — Navin Natnithithadha
Assistant Examiner — Sunita Reddy
(74) Attorney, Agent, or Firm — Hoffmann & Baron, LLP (57) ABSTRACT A sleep induction device includes at least one sensor for detecting a physiological characteristic of the user, a stimulator configured to provide successive stimuli to the user to anticipate on the detected physiological characteristic, which successive stimuli define a guidance path, and which guidance path is to be followed by the user to induce a change during the sleep session of the user, a memory which is arranged to store values of detected physiological characteristics, and provided stimuli during the sleep session, and a processing unit including a control programme which is programmed to determine a current sleep state of the user, which current sleep state is based on at least one detected
(Continued)

physiological characteristic measured by the at least one sensor and which control programme is programmed to generate an initial guidance path to induce a change from the determined current sleep state to another sleep state.

9 Claims, 3 Drawing Sheets

(52) U.S. Cl.
CPC . *A61M 2021/0088* (2013.01); *A61M 2230/06* (2013.01); *A61M 2230/42* (2013.01)

(58) Field of Classification Search
USPC ..................................................... 600/26–28
See application file for complete search history.

(56) References Cited

U.S. PATENT DOCUMENTS

| | | | | |
|---|---|---|---|---|
| 2016/0270948 | A1* | 9/2016 | Hariri | A61B 5/4818 |
| 2016/0331305 | A1* | 11/2016 | Krans | A61B 5/08 |
| 2018/0078197 | A1* | 3/2018 | Ware | A61B 5/4812 |
| 2018/0078198 | A1* | 3/2018 | Reich | A61B 5/746 |
| 2018/0078732 | A1* | 3/2018 | Keshavan | A61B 5/4812 |
| 2018/0078733 | A1* | 3/2018 | Freed | A61B 5/6898 |

FOREIGN PATENT DOCUMENTS

| | | |
|---|---|---|
| WO | 2005/055802 A2 | 6/2005 |
| WO | 2011/083468 A1 | 7/2011 |
| WO | 2014/170881 A1 | 10/2014 |
| WO | 2015/118415 A1 | 8/2015 |
| WO | 2016/121755 A1 | 4/2016 |

OTHER PUBLICATIONS

PCT International Search Report, Application No. PCT/NL2018/050203, dated Jun. 25, 2018.

PCT Written Opinion, Application No. PCT/NL2018/050203, dated Jun. 25, 2018.

PCT International Preliminary Report on Patentability, Application No. PCT/NL2018/050203, dated Aug. 1, 2019.

Japanese Office Action, Application No. 2019-555231, dated Mar. 2, 2020, 12 pages.

* cited by examiner

SLEEP INDUCTION DEVICE AND METHOD FOR INDUCING A CHANGE IN A SLEEP STATE

CROSS-REFERENCE TO RELATED APPLICATIONS

This application is the National Stage of International Application No. PCT/NL2018/050203, filed Apr. 3, 2018, which claims the benefit of Netherlands Application Nos. 2018645, filed Apr. 4, 2017, and U.S. Pat. No. 2,018,883, filed May 10, 2017, the contents of all of which are incorporated by reference herein.

FIELD OF THE INVENTION

The present invention relates to a sleep induction device for inducing changes during a sleep session of a user and a method for inducing a change in a sleep state of a user during a sleep session.

BACKGROUND OF THE INVENTION

U.S. Pat. No. 7,041,049 discloses a method and apparatus for obtaining an efficient sleep and using a sleep time more productively. By monitoring select physiological characteristics of the sleeper, it can be determined which sleep stage the sleeper is in, when the sleeper transitions to a different sleep stage, and whether a sleeper is following the lead of a sleep guidance system. The sleep guidance system provides sensory stimuli to influence a sleep to induce a change. Before effectively using the apparatus, it has to be calibrated, to determine the sleepers physiological and sleep pattern responses to the sensory stimuli during sleep. From this calibration step, a personalized sleeper profile is established. The profile includes stimuli settings to pace and lead the sleeper through its sleep. In use, when the profile is unsuccessful in leading the sleeper to a new sleep stage, the system continues to lead the sleeper until the new sleep stage has been reached.

A drawback of the known apparatus is that the required calibration time is relatively long. For the known apparatus to function efficiently, it must first be learned how a sleeper's physiological characteristic or sleep pattern changes when exposed to sensory stimuli, and what are the optimal durations and patterns for a sleeper's sleep cycle. This learning is performed by calibrating the apparatus.

A further drawback of the known apparatus is that it is not adaptive to a suddenly or incidentally changed user situation. For example, the device is not adaptive to an incidentally changed situation wherein the user has caught a cold. Alternatively, the user may have had a busy day, a late night sports activity, or suffer a jet-lag, after which a remarkably different sleep profile in comparison with a mean or personalised sleep profile results. A bed partner of a user may also influence the mean sleep profile, and a sleep profile generally also differs between for example winter- and summertime. In such changed situations, the known device cannot anticipate sufficiently fast.

SUMMARY OF THE INVENTION

The general object of the present invention is to at least partially eliminate the above mentioned drawbacks and/or to provide a usable alternative. More specifically, it is an object of the invention to provide a sleep induction device that can be used successfully from the first night of use, and/or to provide a sleep inducting device that is adaptive when the sleep profile of a user differs from the mean sleep profile.

This object is achieved by a sleep induction device according to the present invention.

According to the invention, a sleep induction device is provided which is arranged to induce a change during a sleep session of a user. A change during a sleep session means a change from a first sleep state to a second sleep state. The change may for example be a change in a respiration rate during a NREM-sleep stage.

It is noted that a sleep session, in the context of this document, spans the time period from getting ready to sleep, e.g. getting into bed or lying on a couch, until waking up, e.g. getting out of bed or stepping from the couch.

In particular, the sleep induction device is arranged to induce a change, a so called sleep stage transfer, which means a change from a first sleep stage to a second sleep stage, e.g. from a light to a deep sleep stage or from a REM to a NREM sleep stage.

The sleep induction device comprises at least one sensor for detecting a physiological characteristic of the user. Such a physiological characteristic may be a respiration rate, heart rate, body movement or other physiological characteristic which might be of interest to control a sleep profile of the user.

The sleep induction device comprises a stimulator. The stimulator is configured to provide successive stimuli to the user during the sleep session. The stimulator may provide stimuli to the user continuously. The stimulator provides successive stimuli to anticipate on the detected physiological characteristics, to guide the user. In particular, the user is guided by the successive stimuli via a guidance path, the user following the guidance path to induce a change during the sleep session of the user, e.g. to guide a user from a first sleep state of the user to a second sleep state of the user. Preferably, the guidance path is configured to provide a smooth and timely transfer from the first sleep state to the second sleep state. It is noted that this 'following' the guidance path by the user is preferably done subconsciously. It is further noted that a stimulator, in contrast to what a more common meaning of word may be, may be intended to relax the user.

Multiple stimulators may be comprised in the sleep induction device. Multiple stimulators may be active at the same time, the stimulators working in parallel.

The sleep induction device comprises at least one memory for storing data during the sleep session. The memory is arranged to store values of detected physiological characteristics and provided stimuli during the sleep session. The memory may for example compute a historic record of the provided stimuli and the corresponding physiological characteristics. Preferably, this historic record is updated in real-time.

The sleep induction device comprises a processing unit, also called a control unit, for operating the device. The processing unit includes a control program which is programmed to determine a current sleep state of the user during the sleep session. The current sleep state is based on at least one detected physiological characteristic measured by the at least one sensor. The current sleep state may depend on real-time measurements, and may also depend on the historic record of measurements, stored in the memory. For example, when transitioning from a light to a deep sleep, the heart rate of a user may slow down, to rise again when reaching REM sleep. Based on only the real-time measurements, it may be difficult to determine whether the user is awake or in REM sleep. For that reason, the current sleep state may be determined by the real-time measurements in combination with a historic record of measurements.

The control programme is further programmed to generate an initial guidance path to induce a change from the determined current sleep state to another sleep state. The initial guidance path may for example be equal to a previous guidance path that was executed successfully, or may be selected from a number of pre-programmed guidance paths.

Further, the control program comprises a tracking program which is programmed to track during the sleep session a deviation of a detected physiological characteristic from an expected physiological characteristic which expected physiological characteristic is based on the initially provided guidance path or an updated guidance path. Hence, the expected physiological characteristics may be based on the current or real-time activated guidance path. For example, the respiratory rate of a user may have a certain expected trajectory as a function of time, based on the initiated guidance path. The deviation between the measured respiratory rate and the expected respiratory rate may then be tracked by the tracking program.

Further, the control program comprises a tailoring program which is programmed to tailor the initially provided guidance path during the sleep session of the user to an updated guidance path when the tracked deviation exceeds a pre-determined margin. The updated or user-moment-specific guidance path may for example be determined based on at least one of the following values: previously initiated guidance path, real-time effectiveness of the stimuli and the historic record thereof, real-time deviation between detected physiological characteristic and expected physiological characteristic and historic record thereof, historic record of effective guidance paths, and/or historic records of physiological characteristics of the user when said effective guidance paths were initiated. The historic record may span the current sleep session, or a longer period of time.

The tailoring programme may also tailor an updated guidance path during the sleep session of the user to a further updated guidance path when the tracked deviation exceeds a pre-determined margin.

Said pre-determined margin may be user-dependent. For example, embodiments are conceived wherein a user rates the sleep experience after waking up. When it is determined that the user feels that he or she is corrected too quickly, the margin may be set to a larger value.

An advantage of the sleep induction device according to the invention is that it can be used to induce changes already during a sleep session of a user, even from a first time of use. In comparison with the apparatus of U.S. Pat. No. 7,041,049, the sleep induction device according to the invention operates during a sleep session with a guidance path which guidance path is adaptable to another guidance path during the same sleep session. An adaption of the guidance path can be real-time introduced and is not postponed to a next sleep session.

Although there may be a set-up phase in which an initial guidance path is selected based on for example a query, principally no training period is required to transfer knowledge about sleep characteristics of the individual user (including but not limited to preferred sleep profile, physiological characteristics during different sleep stages, efficient stimuli, efficient guiding paths) into the memory of the sleep induction device. The sleep induction device obtains this knowledge during use, and the device will already be adapted to the user during the same sleep session to work more efficient and effective.

A further advantage of the sleep induction device according to the invention is that these adaptive properties may remain present after prolonged use. The sleep induction device may be able to recognize situations in which the sleep profile of the user deviates from the mean or normal sleep profile, adapting the stimuli provided by the stimulator when needed. This is beneficial for users that have irregular sleep sessions, for example due to sleepwalking, getting up at night, e.g. to visit the bathroom or to feed children, the user suffering an illness, having a high blood-alcohol level, or due to any other reason. The sleep induction device recognizes that the current sleep session deviates from a mean sleep session, and will adapt the guiding path accordingly, during the entire night.

Embodiments are conceivable where there is interactivity with the user, for example such that the user can provide feedback. The sleep induction device can then learn, after the user has awoken, whether a deviation in sleep behaviour, if it occurred during a particular night, was an event that occurred only once, or if it can be expected for the next sleep session or sleep sessions as well.

Embodiments are also conceivable where the user can inform the sleep induction device before starting the sleep session that a different sleep profile than the mean sleep profile is expected, for example due to the user having had a stressful day.

In an embodiment of the sleep induction device according to the invention, the tailoring programme selects the updated or initial guidance path from a group of pre-programmed guidance paths. Any number of guidance paths may be pre-programmed. For different changes during a sleep session of a user, different guidance paths may be used. The optimal guidance path is in general highly user-dependent, with some users for example needing more time or a different guiding path to fall asleep than other users.

In an embodiment of the sleep induction device according to the invention, the tailoring programme is programmed to develop novel guidance paths. The tailoring programme may be programmed to render a guidance path by a formula in which the guidance path is a function of the physiological characteristic. The physiological characteristic may be a parameter of a mathematical function to calculate and render the guidance path. This allows to optimally tailor the guidance path to the user, developing a user-specific guidance path.

In an embodiment of the sleep induction device according to the invention, an effectiveness of the initially provided guidance path is rendered by said deviation, and the tailoring programme tailors said initial guidance path when said effectiveness is below a pre-determined margin. The effectiveness may for example be rendered from the real-time deviation, the spread of the deviation over a time period, or the average deviation. Hence, the deviation may not be directly used to initiate the tailoring programme, but may also indirectly be used to initiate the tailoring programme.

In an embodiment of the sleep induction device according to the invention, the change in the sleep session makes a user fall asleep, i.e. the guidance path inducing a change from a fully awakened state to at least a light sleep state. The sleep induction device then helps the user to fall asleep, for example at the start of a sleep session, or after the user has awoken during a sleep session.

In an embodiment of the sleep induction device according to the invention, the sleep state is determined by a single or by multiple physiological characteristics. For example, the heart rate, the respiratory rate, the brain wave activity, the bodily movements, the eye movement, and/or noises produced by the user may be used to determine the sleep state of a user.

In an embodiment of the sleep induction device according to the invention, the device comprises a housing for housing components, and wherein the stimulator comprises a stimulator mechanism for frequently expanding and collapsing a body, to provide a stimulating rhythm to the user to influence the users respiration rate. The body may for example be formed as a pillow or mattress, wherein the body has a soft outer skin. The user can for example spoon the body in user.

However, any stimulator can be used to provide stimuli to the user, the stimulator being external of the body of the user, or the stimulator being applied to the body of the user, wherein there may be multiple stimulators.

The invention further relates to a method for inducing a change in a sleep state of a user during a sleep session, using a sleep induction device as described in the above, the method comprising the steps of:

monitoring at least one physiological characteristic of the user during the sleep session;

storing values of detected physiological characteristics of the user during the sleep session;

determining a current sleep state of the user based on at least one monitored physiological characteristic, for example based on historic data;

stimulating the user by providing successive stimuli which form an initial guidance path to guide the user from a first sleep state to a second sleep state, such that a change in the sleep state of the user is induced;

storing values of the provided initial guidance path during the sleep session and updating the historic data;

tracking during the sleep session a deviation between a detected physiological characteristic and an expected physiological characteristic, which expected physiological characteristic is based on the initially provided guidance path or the updated guidance path;

in case that the tracked deviation of the initially provided guidance path exceeds a pre-determined margin, tailoring the initially provided guidance path to an updated guidance path during the same sleep session.

In an embodiment of the method according to the invention, the step of tailoring the initially provided guidance path to an updated guidance path includes a step of synchronising the sleep induction device with the user, which synchronising includes iterating steps of:

selecting a different guidance path to stimulate the user by providing different successive stimuli;

tracking a deviation between a detected physiological characteristic and an expected physiological characteristic based on the currently provided different guidance path, wherein:

in case the deviation still exceeds a pre-determined margin, repeating the step of selecting and tracking with yet another, different, guidance path;

in case of a reduced deviation, rendering the updated guidance path;

continuing the method during the sleep session with the updated guidance path.

BRIEF DESCRIPTION OF THE DRAWINGS

The invention will be explained in more detail with reference to the appended drawings. The drawings show a practical embodiment according to the invention, which may not be interpreted as limiting the scope of the invention. Specific features may also be considered apart from the shown embodiment and may be taken into account in a broader context as a delimiting feature, not only for the shown embodiment but as a common feature for all embodiments falling within the scope of the appended claims, in which:

DETAILED DESCRIPTION OF THE INVENTION

Figure 1:
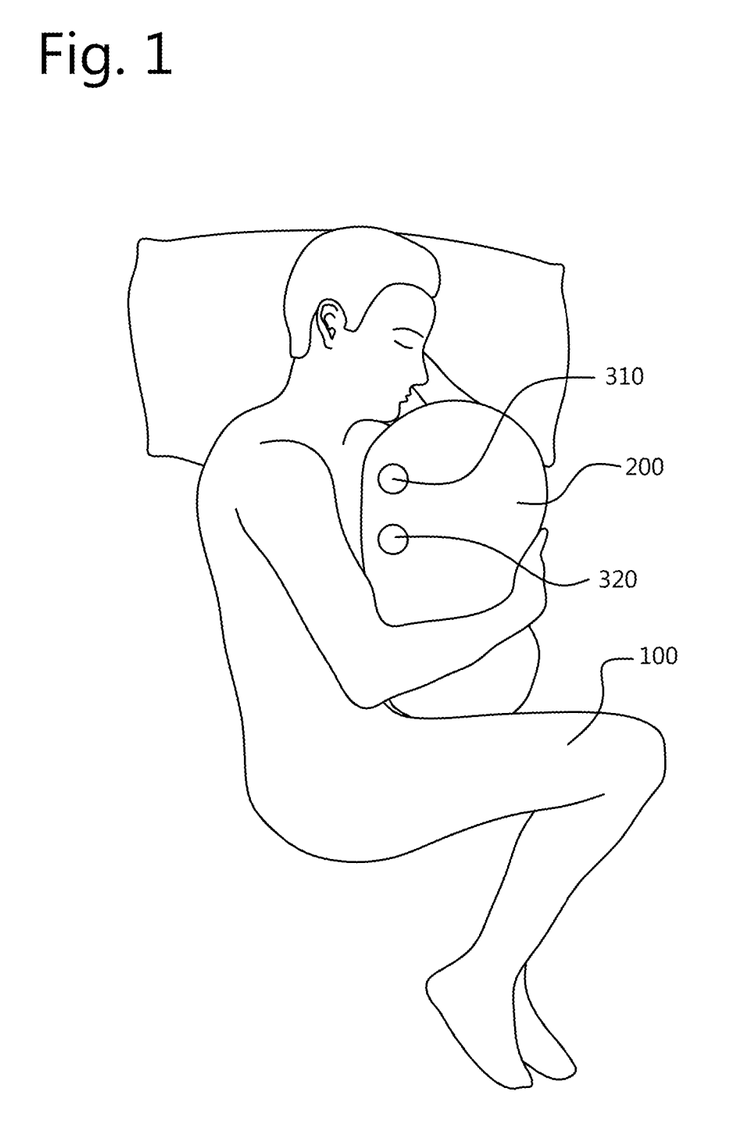
FIG. 1 schematically shows a sleep induction device according to the invention and a user.

Shown in FIG. 1 is an embodiment of a sleep induction device for inducing changes during a sleep session of a user 100, the sleep induction device comprising a stimulator body 200 and two sensors for detecting a physiological characteristic of the user 100: a heart rate monitor 310, and a respiratory rate monitor 320. In the embodiment of FIG. 1, the stimulator body 200 comprises a stimulator mechanism (not visible) for frequently expanding and collapsing the stimulator body, to provide a stimulating rhythm to the user to influence the users respiration rate. The sleep induction device further comprises a housing for housing components e.g. electrical components.

More specifically, the sleep induction device of FIG. 1 has a stimulator body which is formed as a peanut-shaped pillow, wherein the stimulator body has a soft outer skin, the sleep induction device being configured to simulate a breathing rhythm of a person by alternate contraction and expansion. Many alternative stimulator bodies can however be used, stimulating the user in many different ways, including via light, sound, vibration, temperature changes, or with other stimuli that can be experienced by the user.

When the device comprises the peanut-shaped pillow visible in FIG. 1, a user using the sleep induction device preferably lies in bed during a sleep session, spooning the pillow or holding it closely to its body.

Further, the sleep induction device comprises a memory, arranged to store values of detected physiological characteristics and provided stimuli during the sleep session and a processing unit.

Further, the sleep induction device comprises a processing unit including a control programme which is programmed to determine a current sleep state of the user, which current sleep state is based on at least one detected physiological characteristic measured by the at least one sensor and which control programme is programmed to generate an initial guidance path to induce a change from the determined current sleep state to another sleep state. The control programme comprises a tracking programme that is programmed to track during the sleep session a deviation of a detected physiological characteristic from an expected physiological characteristic which expected physiological characteristic is based on the initially provided guidance path, and a tailoring programme which is programmed to tailor the initially provided guidance path during the sleep session of the user to an updated guidance path when the tracked deviation exceeds a pre-defined margin. The memory and processing unit can for example be arranged inside the stimulator body 200. The processing unit may receive input from the heart rate 310 and respiratory rate 320 monitors, and may determine the sleep state of the user based upon those inputs.

The sleep induction device is able to influence the sleep state of the user by inducing changes, stimulating the user with successive stimuli and defining a guidance path via said successive stimuli. This guidance path is for example defined by a simulated breathing rhythm of the stimulator, in a way that is better understood with reference to FIG. 2.

Figure 2:
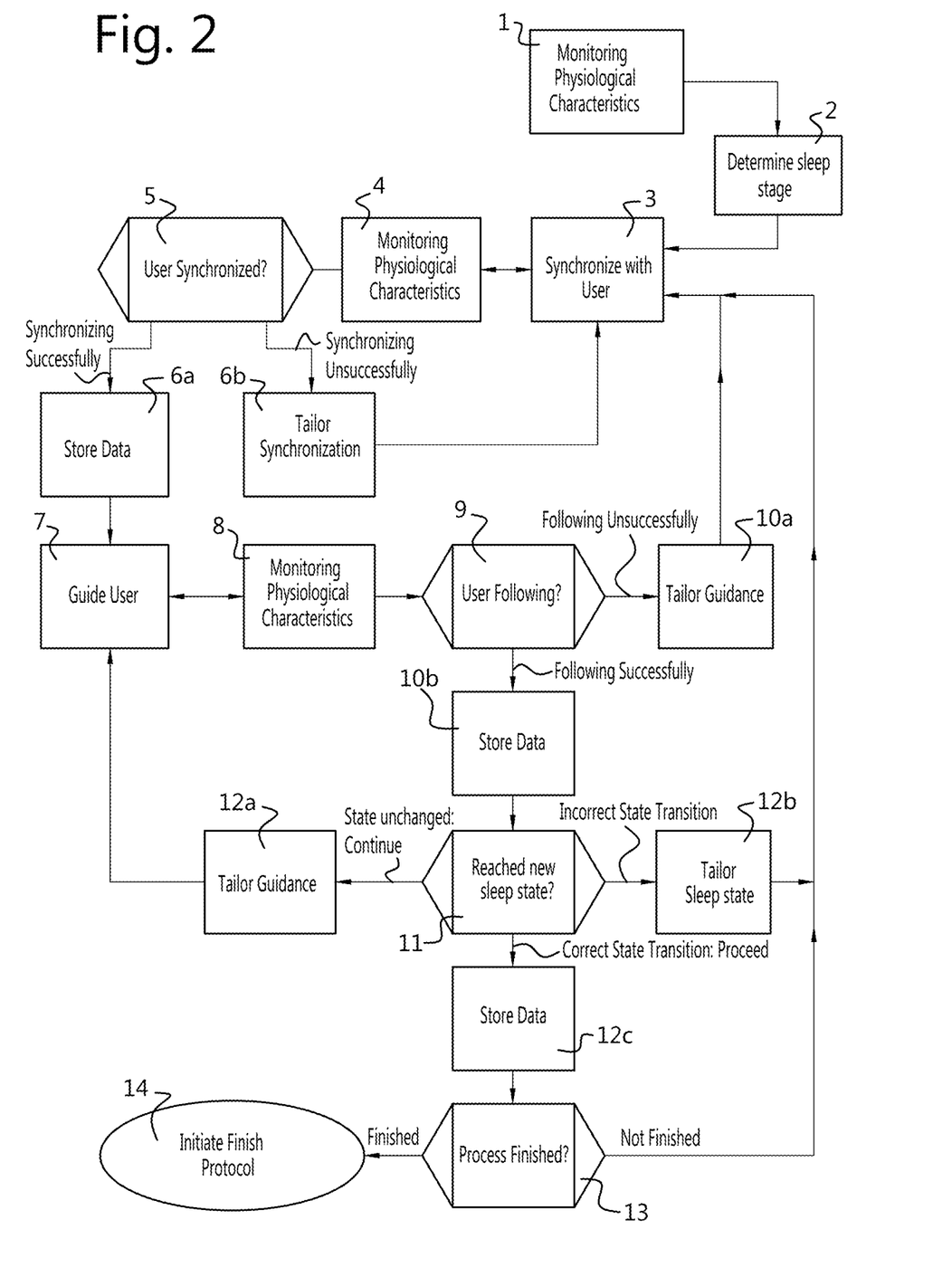
FIG. 2 shows a flow diagram of a method for using the sleep induction device according to an embodiment of the present invention.

Shown in FIG. 2 is a flow diagram of an exemplary method of the sleep induction device, for inducing a change in a sleep state of a user during a sleep session. As a first, after use non-reoccurring and non-shown, step, a set-up phase may be defined. This stage is typically executed only once before start of use, although it may be executed any number of times. In the set-up phase, a pre-programmed guidance path may be selected for a particular user. Any number of guidance paths may be programmed into the sleep induction device, offering various guidance paths to be followed by the user when using the sleep induction device. In the set-up stage, one of the various guidance paths may be selected as an initial guidance path. The set-up stage may be very minimal and only require answering some questions about, for example, preferred sleep position, estimated time between getting in bed and falling asleep, desired amount of sleep per night, and heart rate in rest. Optionally, some questions may be also asked to the partner of the user, such as questions related to the frequency of position changes, sleepwalking, and/or talking in the sleep.

Alternatively or additionally, the set-up stage may include wearing the sensors of the sleep induction device during one or several sleep sessions without the stimulator being activated, e.g. for sleep session spanning up to a week or longer, such that the natural guidance path of a person can be measured, and such that an appropriate guidance path can be selected.

When used, the sleep induction device starts with monitoring at least one physiological characteristic of the user, step 1 of FIG. 2. These physiological characteristics may for example include measuring the heart rate, the respiratory rate, the eye movement, noise produced, body temperature, brain wave pattern, or other physiological characteristics.

The values of the detected physiological characteristics of the user during the sleep session are stored in the memory of the sleep induction device.

Based on these monitored physiological characteristics, a sleep state is determined. A single physiological value may be used, or multiple physiological values may be used to determine said sleep state. Often-used sleep stages include full awakeness, non-rapid eye movement sleep (NREM), and rapid eye movement sleep (REM). The NREM sleep can further be categorized in four sleep stages: NREM 1, NREM 2, NREM 3, NREM 4. A multitude of these six sleep stages may be defined as sleep states for each individual user. As such, the term 'sleep state' does not only include the six sleep stages recognized in the sleep literature, but also more refined states in between these stages, personal to a user. As stated before, a change in sleep state is thus not only limited to a change in sleep stage, but may, for example, also include a change in the respiratory rate of the user in REM sleep, changing the state of the user.

When the sleep state is determined, two successive loops are executed by the sleep induction device.

In the next step, entering the first loop, the user and the stimulator are synchronized or paced with each other, for example by adapting the stimulation rate of the stimulator to the respiratory rate of the user. In general, it is not necessary that the sleep state of the user changes in the pacing phase, although this may be possible.

If the user, after a continued amount of time, does not synchronize with the stimulation device, the values of the monitored physiological characteristics are stored in the memory of the sleep induction device, in combination with the knowledge that the applied synchronization algorithm was not effective (step 6*b*). A new synchronization algorithm is then developed, i.e. the synchronization algorithm is tailored. This first loop of synchronizing the user and the stimulator with each other is iterated, until the stimulator synchronizes with the user, or vice versa, each time storing the effectiveness of the synchronization algorithm.

When it is determined that the user and the stimulator are synchronized, the second loop is entered, inducing changes in the sleep state of a user during a sleep session, and stimulating a user to follow a guidance path, preferably subconsciously.

By stimulating the user with successive stimuli, an initial guidance path is formed to guide the user from a first sleep state to a second sleep state, such that a change in the sleep state of the user is induced. This change in the sleep state of the user can for example be achieved by gradually lowering the respiratory rate simulated by the stimulator, e.g. in continuous or incremental steps. For example, in guiding the user from full awakeness to NREM 1 sleep, the respiratory rate simulated by the stimulation device may be changed slowly, over the course of several minutes or even longer, from 10 breaths per minute to 8 breaths per minute. This stimulates the user to lower the breathing frequency, and induces sleep, lowering the sleep onset latency of the user. During the guiding phase, the physiological characteristics are continuously monitored, to determine if the sleeper is following the guidance path initiated by the stimulator.

The values of the provided initial guidance path and the monitored physiological characteristics are stored in a memory while providing the initial guidance path during the sleep session of the user.

From these stored values, a deviation between a detected physiological characteristic and an expected physiological characteristic can be tracked, wherein the expected physiological characteristic is based on the initially provided guidance path.

Once it is established that the user is following, i.e. the respiratory rate of the user follows the respiratory rate of the stimulation device with a deviation that is smaller than a pre-determined margin, the specific parameters, e.g. the measured heart rate and respiratory rate, the simulated respiratory rate and rate of change in simulated respiratory rate of the stimulation device, and the time it took until the user reached the desired sleep state, are stored in the memory of the sleep induction device, in combination with a value or values indicating the effectiveness of the applied guidance path.

If the user however, after a continued amount of time, does not follow the stimulation device, i.e. when the tracked deviation of the initially provided guidance path exceeds a pre-determined margin, said specific parameters may be stored in the memory of the sleep induction device, in combination with the knowledge that the applied guidance path was not effective.

In considering the deviation between the expected physiological characteristic and the measured physiological characteristic, an effectiveness of the initially provided guidance path may be rendered from the determined deviation. The tailoring programme of the control programme may then tailor the initial guidance path when said effectiveness drops below a pre-defined margin.

Instead of continuing to stimulate the user with stimuli that are not effective, taking the risk that the user is guiding in the wrong direction, such as more towards awakening when a deeper sleep is desired, the initially provided guidance path of the user can be tailored to an updated guidance path already during the sleep session, i.e. during the same sleep session.

This updated guidance path may be selected from a group of pre-programmed guidance paths, or the tailoring programme may be programmed to develop novel guidance paths.

Hence, the sleep induction device does not rigidly follow the initiated guidance path, but adapts the guidance path and creates a different, tailored guidance path when the tracked deviation of the initially provided guidance path exceeds a pre-determined margin.

FIG. 2 will now be explained using a specific example wherein the sleep onset latency of a user is reduced, wherein the sleep induction device is hence used by the user to fall asleep faster. In the below description, the user will be guided from a fully awakened sleep stage to a NREM 1 sleep stage, wherein the user is sleeping lightly, thus changing the sleep state of the user. The change in the sleep session thus makes the user fall asleep, the guidance path inducing a change from a fully awakened state to at least a light sleep state. In this example, the user is familiar with the use of the sleep induction device and the sleep induction device is already set up at a previous time, such that synchronizing, i.e. the first loop described above, is executed relatively fast.

When the user steps into bed, e.g. to start a night of sleep, the sensors are activated and start detecting the physiological characteristics of the user. For example, a heart rate monitor and a respiration monitor can be used. The monitors monitor the physiological characteristics of the user and determine that the user is fully awake. To make the user fall asleep, the user is first paced, to relax the user and to synchronise the stimulator with the user. For example, the stimulator may simulate a respiratory rate of 10 breaths per minute, for a continued period of time, e.g. 2-10 minutes. While pacing the user, the heart and respiratory rate of the user are continuously monitored, to determine if the user is synchronizing with the stimulator.

Once it is established that the user and the stimulator are synchronizing, the initially measured heart and respiratory rate, the applied respiratory rate of the stimulator, and the time it took until the user synchronized are stored in the memory of the sleep induction device.

Figure 3:
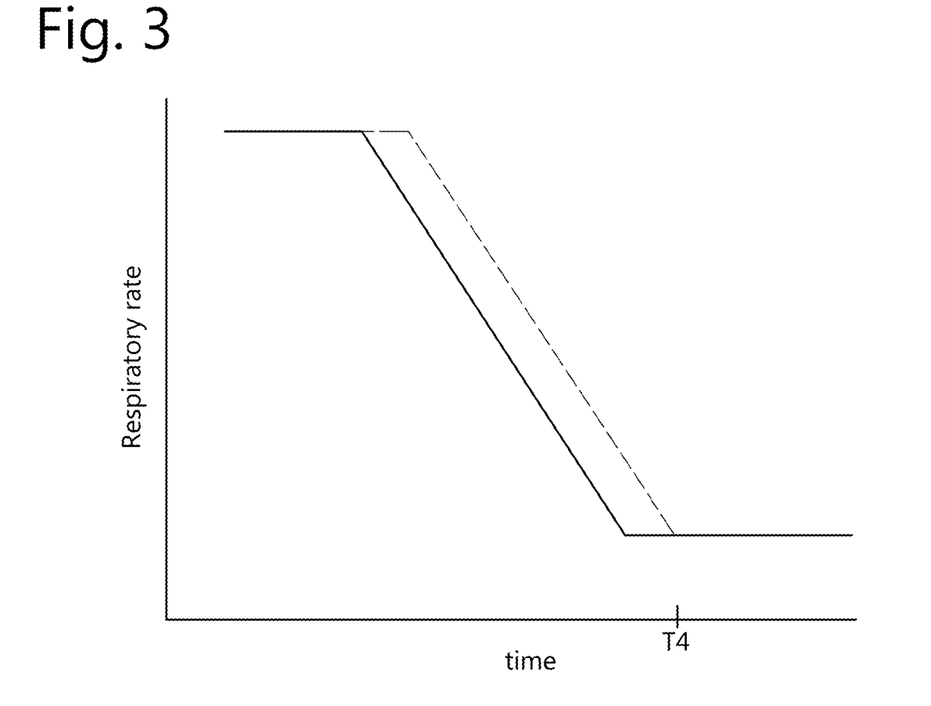
FIG. 3 schematically shows a guidance path to guide the user from a first sleep state to a another sleep state.

In the next step, the sleeper can be guided from a fully awakened sleep stage to the NREM 1 sleep stage, changing the sleep state of the user. For example, with reference to FIG. 3, when the user has been using the sleep induction device successfully for some time, it may be found that it normally takes between 5 and 10 minutes, once the user is synchronizing with the stimulator, to lead the sleeper from full awakeness to NREM 1 sleep, via a guidance path or leading algorithm that gradually decreases the breathing frequency. This preferred guidance path, when the night can be categorised as 'normal', or 'ordinary' is visualized in FIG. 3, where the vertical axis represents respiratory rate, as a function of time. In FIG. 3, the solid line indicates the respiratory rate of the stimulator, while the dashed line indicates an exemplary respiratory rate of a user. In this example, the respiratory rate of the user lags with respect to the respiratory rate of the stimulator, but in general nicely follows the rate of the stimulator, the tracked deviation thus being relatively small. At timestamp T4, the user has transitioned from a fully awakened sleep stage, to a light sleep stage.

It is noted that, for one particular user, the guidance path as shown in FIG. 3 may be considered the optimal guidance path, under normal conditions. However, for a different user, this guidance path may not work. Many different guidance paths can be envisioned, and preferably a multitude of guidance paths is pre-programmed into the sleep induction device, such that a particular user can experiment with different guidance paths and determine which guidance path works best.

Figure 4:
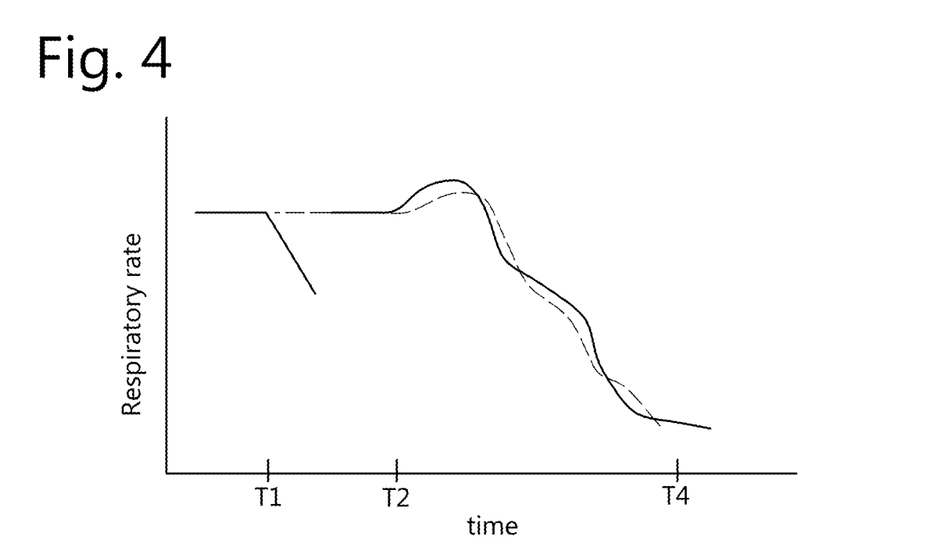
FIG. 4 schematically shows an alternative guidance path to guide the user from a first sleep state to a another sleep state

Shown in FIG. 4 is a situation where the user does not follow the initiated guidance path in a satisfactory way, for a continued amount of time. There can be many reasons why a sleeper does not follow the normal, preferred guidance path, including but not limited to: the user suffering a cold or other illness, the partner of the user suffering a cold or another illness, a higher than normal environment noise, a higher blood alcohol level, the user having has a stressed day, the user having had a relaxed day, the sleep induction device not sufficiently being adapted to the specific preferences of the user enough, etc.

In FIG. 4, the respiratory rate of the user is again shown by a dashed line, while the respiratory rate of the stimulator is shown by a solid line.

At time T1 in FIG. 4, it is recognized by sleep induction device that the user no longer follows the initiated guidance path, i.e. the deviation with respect to the initially provided guidance path exceeds a pre-determined margin. The initially activated guidance path is stopped at time T1, and an updated, tailored, guidance path, is initiated during the same sleep session. This may be done directly at time T1, or the sleep induction device may wait a while to observe the natural sleep behaviour of the user.

This newly determined, tailored guidance path follows a path that is different from the initial guidance path. For example, the initial guidance path, the one that was shown in FIG. 3, may gradually decrease the respiratory rate from 10 breaths per minute to 8 breaths per minute in 8 minutes, following a linear, continuous decrease in respiratory rate. The updated guidance path may for example be slower, faster, or non-linear, such as sinusoidal, continuously decreasing, or follow a step-wise approach.

In FIG. 4, when it is observed that the user is not following the initial guidance path, the user is synchronized again, as can be observed from FIG. 2. This may take some time, for example until time T2. At time T2, the updated guidance path is initiated, guiding the user towards a different sleep state. In the example indicated in FIG. 4, the updated guidance path at first gradually increases the breathing rate of the user, after which said rate is decreased again. In the example of FIG. 4, this tailored guidance path is effective and the user reaches the new sleep state at time T4.

With reference to FIG. 2, the step of tailoring the initially provided guidance path to an updated guidance path includes a step of synchronising the sleep induction device with the user. This synchronisation loop includes iterating steps of selecting a different guidance path to stimulate the user by providing different successive stimuli, and tracking a deviation between a detected physiological characteristic and an expected physiological characteristic based on the currently provided different guidance path.

In the case that the deviation still exceeds a pre-determined margin, the steps of selecting and tracking are repeated with yet another, different, guidance path.

In the case that the deviation is reduced with the updated guidance path, the updated guidance path is applied.

After updating the guidance path, the method is continued with the updated guidance path, while the sleep session is uninterrupted.

With reference to FIG. 2, it was shown in FIGS. 3 and 4 how an initial guidance path was initiated, and that the physiological characteristics of the user were monitored while the guidance path is executed. When the initial guidance path is effective, the situation of FIG. 3, it is determined that the user is following the respiratory rate dictated by the stimulator, and a new sleep state is quickly reached. This is then stored, and the process may be finished.

In the situation or FIG. 4, a guidance path is also initiated, and physiological characteristics of the user are also measured. However, in the situation of FIG. 4, the user is not following the initiated guidance path, and an updated guidance path is initiated, after which the user and the stimulator are is synchronized again.

When an updated guidance path was established during a sleep session, and when a person wakes up for a second time during the same sleep session, for example after a bathroom visit or because the sleep session is disturbed by an external factor such as noise, light, etc., the updated guidance path can immediately be executed, as it was stored in the memory that the initial guidance path was not effective.

It is noted that the term "comprising" (and grammatical variations thereof) is used in this specification in the inclusive sense of "having" or "including", and not in the exclusive sense of "consisting only of".

It is further noted that features and aspects described for or in relation with a particular embodiment may be suitably combined with features and aspects of other embodiments, unless explicitly stated otherwise.

Although the invention has been disclosed with reference to particular embodiments, from reading this description those of skilled in the art might appreciate a change or modification that may be possible from a technical point of view but which still do not depart from the scope of the invention as described above and claimed hereafter.

It will be understood by those of skilled in the art that various changes may be made and equivalents may be substituted for elements thereof without departing from the scope of the invention. It is in particular possible to make modifications with respect to the illustrated embodiments which are provided as exemplary embodiments. Modifications may be made within the teaching of the invention and without departing from the scope thereof to adapt a particular situation.

Therefore, the invention is not limited to the particular embodiments disclosed and illustrated in the above detailed description, but the invention will include all embodiments falling within the scope as described above and defined in the appended claims.

The invention claimed is:

1. A sleep induction device for inducing changes during a sleep session of a user, wherein the sleep induction device comprises:
   at least one sensor for detecting at least one physiological characteristic of the user;
   a stimulator which is configured to provide successive stimuli to the user to operate based on the at least one detected physiological characteristic, which successive stimuli define a guidance path, and which guidance path is to be followed by the user to guide the user in a transfer from a first sleep state to a second sleep state;
   a memory which is arranged to store values of the at least one detected physiological characteristic, and provided stimuli during the sleep session;
   a processing unit including a control program which is programmed to determine a current sleep state of the user, which current sleep state is based on the at least one detected physiological characteristic measured by the at least one sensor and which control program is programmed to generate an initial guidance path to induce a change from the determined current sleep state to another sleep state;
   wherein the control program comprises
   a tracking program which is programmed to continuously monitor the physiological characteristic during a guiding phase to determine whether the user is
   following the initial guidance path by tracking a deviation of the at least one detected physiological characteristic from an expected physiological characteristic which expected physiological characteristic is based on the provided initial guidance path;
   a tailoring program which is programmed to tailor the provided initial guidance path in real-time during the same sleep session of the user to an updated guidance path in the case that the tracked deviation exceeds a pre-determined margin; and
   wherein an effectiveness of the provided initial guidance path is calculated based upon said deviation, and wherein the tailoring program tailors said initial guidance path in the case that said effectiveness is below a pre-defined margin.

2. The sleep induction device according to claim 1, wherein the tailoring program selects the updated guidance path from a group of pre-programmed guidance paths.

3. The sleep induction device according to claim 1, wherein the tailoring program is programmed to render the updated guidance path by a formula in which the guidance path is a function of the physiological characteristic.

4. The sleep induction device according to claim 1, wherein said change in the sleep session makes the user fall asleep.

5. The sleep induction device according to claim 1, wherein the current sleep state is determined by a single or by multiple physiological characteristics.

6. The sleep induction device according to claim 1, wherein the device comprises a housing for housing components, and wherein the stimulator comprises a stimulator mechanism for frequently expanding and collapsing a body, to provide a stimulating rhythm to the user to influence a user's respiratory rate.

7. The sleep induction device according to claim 6, wherein said body is formed as a pillow, wherein the housing has a soft outer skin.

8. A sleep induction device for inducing changes during a sleep session of a user, wherein the sleep induction device comprises:
   at least one sensor for detecting at least one physiological characteristic of the user;
   a stimulator which is configured to provide successive stimuli to the user to operate based on the at least one detected physiological characteristic, which successive stimuli define a guidance path, and which guidance path is to be followed by the user to guide the user in a transfer from a first sleep state to a second sleep state;
   a memory which is arranged to store values of the at least one detected physiological characteristic, and provided stimuli during the sleep session;

a processing unit including a control program which is programmed to determine a current sleep state of the user, which current sleep state is based on the at least one detected physiological characteristic measured by the at least one sensor and which control program is programmed to generate an initial guidance path to induce a change from the determined current sleep state to another sleep state;

wherein the control program comprises a tracking program which is programmed to continuously monitor the physiological characteristic during a guiding phase to determine whether the user is following the initial guidance path by tracking a deviation of the at least one detected physiological characteristic from an expected physiological characteristic which expected physiological characteristic is based on the provided initial guidance path;

a tailoring program which is programmed to tailor the provided initial guidance path in real-time during the same sleep session of the user to an updated guidance path without switching to another sleep pattern in the case that the tracked deviation exceeds a pre-determined margin.

9. A sleep induction device for inducing changes during a sleep session of a user, wherein the sleep induction device comprises:

at least one sensor for detecting at least one physiological characteristic of the user;

a stimulator which is configured to provide successive stimuli to the user to operate based on the at least one detected physiological characteristic, which successive stimuli define a guidance path, and which guidance path is to be followed by the user to guide the user in a transfer from a first sleep state to a second sleep state;

a memory which is arranged to store values of the at least one detected physiological characteristic, and provided stimuli during the sleep session;

a processing unit including a control program which is programmed to determine a current sleep state of the user, which current sleep state is based on the at least one detected physiological characteristic measured by the at least one sensor and which control program is programmed to generate an initial guidance path to induce a change from the determined current sleep state to another sleep state;

wherein the control program comprises a tracking program which is programmed to continuously monitor the physiological characteristic during a guiding phase to determine whether the user is following the initial guidance path by tracking a deviation of the at least one detected physiological characteristic from an expected physiological characteristic which expected physiological characteristic is based on the provided initial guidance path;

a tailoring program which is programmed to tailor the provided initial guidance path in real-time during the same sleep session of the user to an updated guidance path while maintaining a predetermined sleep pattern in the case that the tracked deviation exceeds a pre-determined margin.

* * * * *